United States Patent [19]
Chaudhry et al.

[11] Patent Number: 5,804,202
[45] Date of Patent: *Sep. 8, 1998

[54] THICKENERS FOR PRODUCTS FOR TOPICAL APPLICATION

[75] Inventors: Arshad-Ul-Haq Chaudhry, Wellingborough; Roman J. Mikolajewicz, Rushden, both of Great Britain

[73] Assignee: Scott Bader Company Limited, Wellingborough, England

[ * ] Notice: The term of this patent shall not extend beyond the expiration date of Pat. No. 5,688,514.

[21] Appl. No.: 95,475

[22] Filed: Jul. 22, 1993

Related U.S. Application Data

[63] Continuation of Ser. No. 847,739, Mar. 9, 1992, abandoned.

[30]   Foreign Application Priority Data

Mar. 9, 1992 [GB] United Kingdom ................. 9104878

[51] Int. Cl.$^6$ ................................ A61K 7/48; A61K 9/10
[52] U.S. Cl. ..................... 424/401; 424/59; 424/70.1; 424/70.16; 424/73; 424/78.03; 424/78.07; 424/401; 424/405; 424/487; 424/488; 514/938; 524/555
[58] Field of Search ............... 424/401, 70, 405, 424/70.1, 487, 488, 59, 70.16, 73, 78.03, 78.07; 514/938, 942; 524/555

[56]    References Cited

U.S. PATENT DOCUMENTS

| | | | |
|---|---|---|---|
| 4,443,576 | 4/1984 | Bhattacharyya et al. | 524/522 |
| 4,690,996 | 9/1987 | Shih et al. | 523/130 |
| 4,722,958 | 2/1988 | Sauer et al. | 524/379 |
| 4,748,220 | 5/1988 | Hartmann et al. | 526/89 |
| 4,806,345 | 2/1989 | Bhattacharyya | 424/70 |
| 4,994,088 | 2/1991 | Ando et al. | 524/401 |

FOREIGN PATENT DOCUMENTS

| | | |
|---|---|---|
| 0173033 | 3/1986 | European Pat. Off. . |
| 0186361 | 7/1986 | European Pat. Off. . |
| 0196162 | 10/1986 | European Pat. Off. . |
| 0239035 | 9/1987 | European Pat. Off. . |
| 186361 | 9/1990 | European Pat. Off. . |
| 2400587 | 3/1979 | France . |
| 2007238 | 5/1979 | United Kingdom . |
| 2077750 | 12/1981 | United Kingdom . |
| 2206125 | 12/1988 | United Kingdom . |

*Primary Examiner*—Neil S. Levy
*Attorney, Agent, or Firm*—Pillsbury Madison & Sutro LLP

[57]    ABSTRACT

A thickener for products for topical application such as personal care products for application to the skin or hair, or topically administrable pharmaceutical preparations, comprises a water-in-oil emulsion containing polymeric material, at least 98% of which polymeric material is soluble in the aqueous phase. The polymeric material comprises units derived from (a) acrylamide, (b) 2-acrylamido-2-methylpropane-sulphonic acid (AMPS) and (c) a polyfunctional monomer, present in an amount of from 0.12 to 2 milliequivalents per mol of total monomer units. At least some of the AMPS units are in the form of a neutral salt such that the aqueous phase of the water in oil emulsion has a pH of at least 5.5.

23 Claims, 1 Drawing Sheet

THICKENERS FOR PRODUCTS FOR TOPICAL APPLICATION

This is a continuation of application Ser. No. 07/847,739, filed on Mar. 9, 1992.

FIELD OF THE INVENTION

This invention relates to water soluble polymer compositions specifically tailored for use as thickeners/stabilizers for products for topical application such as personal care products for application to the skin or hair, or topically administrable pharmaceutical preparations, where the formulated products are of an anionic or nonionic character.

BACKGROUND OF THE INVENTION

Personal care products are those applied to the skin and/or hair, examples of which are moisturizers, cleansers, toners, barrier creams, shampoos, and styling and setting gels. Such products are usually formulated as creams (oil in water emulsions), or clear gels which may contain substantial quantities of water miscible alcohols or glycols. All use thickeners/stabilizers to modify rheological properties and to improve stability.

Conventionally both natural and synthetic materials have been used for this purpose. Natural products (eg gum arabic, guar gum or starches) vary in quality and hence performance. They also result in products of only a limited shelf life. Synthetic materials are more commonly used having a more consistent quality giving products of better stability. Currently used synthetics are all solids or powders of polymers having residual acid groups, which have to be dispersed or dissolved in water then neutralised before becoming effective. This is because the thickening capability of such compounds is pH dependent; they will not thicken until the acid groups have been neutralised. Great care is needed to prevent agglomeration and lump formation; hours of mixing may be needed before a stable dispersion is achieved.

A significant advantage for the personal care products and pharmaceuticals industry would be to provide a polymer composition which would serve both as a thickener and as a stabilizer and was also in liquid form to enable easy handling by automatic dispensers, metering pumps etc, and which is readily dispersible.

SUMMARY OF THE INVENTION

Surprisingly, we have found that it is possible, by the present invention and using the well known inverse polymerisation technique, to produce polymers that function as both thickeners and stabilizers. They are dispersible in seconds and fully effective without neutralisation, yet still conform to all other stringent conditions ideally required for these specific applications, ie:

1) Do not impede the fully formulated personal care or pharmaceutical product from meeting all statutory safety and toxicological requirements for use.
2) Are highly efficient, ie the maximum addition which would serve both as a thickener and stabilizer should represent $\leq 2.0\%$, preferably $\leq 1.5\%$ and most preferably $\leq 1.0\%$ (expressed as polymer solids) of the total composition. At room temperature, in de-ionized water at a concentration of 2% by weight, a viscosity equal to or greater than 30,000 mPa.s should be achieved. Viscosity is measured on a UK LVF viscometer spindle 4 speed 6.
3) Are effective thickeners and stabilizers and show minimal viscosity change over a wide pH range of about 4 to 14, especially 5 to 10 and most importantly 5 to 9. This is because personal care products preferably have a pH range of between 5 and 9.0, and most preferably between 5.5 and 7.5. Polymers useful in this invention when measured as a 1% (polymer solids) solution, in deionised water, have a pH $\geq 5.5$ and most preferably $\geq 6.0$ but $\leq 10.0$.
4) Have an especially high content of water soluble polymer ie $\geq 98.0\%$, preferably $\geq 99.0\%$ and most preferably $\geq 99.5\%$. The solubility assessment is made by vacuum filtering 2 liters of 0.1% aqueous thickener solution (expressed as polymer solids) through a 46 micron screen, washing the residue, then drying at 110° C. to constant weight. This high solubility allows essentially all of the polymer to be dissolved in the liquid phase of the personal care or pharmaceutical product.
5) Once formulated the polymer remains water soluble so that it can easily be washed off the skin.
6) Molecular weight of the polymer should be high enough to prevent the polymer's absorption through the skin (say $\geq 500,000$), but low enough to maintain high water solubility (say $\leq 10M$, especially $\leq 5M$). This is characterised by the polymer viscosity requirement in combination with the toxicological testing of the fully formulated product.
7) Are able to thicken and stabilize aqueous alcohol and/or glycol solutions.
8) Possess oil emulsification properties as oily substances are often used in cream formulations eg sweet almond oil, paraffin oil and cetearyl octanoate.
9) Be UV and temperature stable under all normal conditions of use; when considering barrier creams for skiers, this extends below 0° C. A suitable accelerated test at higher temperature would be stability of at least 1 month at 50° C. in a fully formulated composition.
10) Formulated products should be smooth and free of lumpy or gritty components. They should be neither sticky nor adhesive in character.

According to a first aspect, the invention provides a water in oil emulsion containing polymeric material, in which at least 98% of the polymeric material in the emulsion is water soluble, and the polymeric material comprises units derived from (a) acrylamide (b) 2-acrylamido-2-methylpropanesulphonic acid (AMPS which is a registered trade mark of the Lubrizol Corp.), and (c) a polyfunctional monomer in an amount of from 0.12 to 2 milliequivalents inclusive per, mole of total monomer units, at least some of the AMPS units being in a neutral salt form, such that the aqueous phase of the water in oil emulsion has a pH of at least 5.5.

According to a second aspect, the invention provides a method of preparing a composition for topical application, which method comprises admixing a topically acceptable, liquid-containing, formulation containing a topically acceptable adjuvant with a water in oil emulsion as defined above. The formulation to which the water in oil, polymer containing, emulsion is added is preferably at least mainly liquid.

The invention additionally provides, according to a third aspect, a composition for topical application comprising
  a topically acceptable liquid phase comprising an aqueous medium,
  a polymeric material at least 98% of which is water soluble, which polymeric material comprises units derived from (a) acrylamide, (b) 2-acrylamido-2-methylpropanesulphonic acid and (c) a polyfunctional monomer, which polyfunctional monomer is present in an amount of from 0.12 to 2 milliequivalents inclusive per mole of total monomer units, an oil phase, a water in oil emulsifier, an oil in water emulsfier, and a topically acceptable adjuvant, optionally forming part of the liquid phase.

In particular, the invention provides a personal care product in which the topically acceptable liquid phase additionally comprises an aqueous alcohol and/or glycol solution, and also provides a pharmaceutical composition for topical application (which may additionally be a personal care product) in which the above composition for topical application contains additionally a pharmaceutically active component.

The water in oil emulsion may be prepared by a method, according to yet another aspect of the invention, which method comprises forming a water in oil emulsion of a monomer composition, in which the concentration of total monomer by weight of the total water in oil emulsion thereof is at least 30 weight % and which monomer composition comprises (a) acrylamide (b) AMPS and (c) a polyfunctional monomer in an amount of from 0.12 to 2 milliequivalents per mole of total monomer composition, at least some of the AMPS being in a neutral salt form, such that the aqueous phase of the water in oil emulsion has a pH of at least 5.5, and subjecting the monomer composition in the said emulsion to polymerisation.

The water in oil emulsion of the polymer can be obtained by the inverse emulsion polymerisation reaction of the neutralised salt of AMPS with acrylamide. They are reacted simultaneously with a small amount of the crosslinking agent to produce a partially crosslinked structure which is still water soluble. As the copolymers are derived from anionic and nonionic monomers they are compatible, and hence effective, in formulated systems of either anionic or nonionic character.

A similar combination of monomers, using $N,N^1$-methylene-bisacrylamide (MBA) as the crosslinker, is disclosed in GB-B-2007238. Although no method of determining water solubility is given, this combination is said to produce polymeric material which is a mixture of water insoluble (ie swellable) and water soluble polymers, at least 40% of which mixture is water insoluble. This mixture is chosen so as to provide improved Theological properties in the presence of electrolyte. However, such polymeric materials could not be formulated into a cream or gel of equivalent smoothness to that achievable using water soluble polymers of the present invention.

Polymers useful in the present invention can be manufactured by the processes disclosed in GB-B-2206125 and EP-B-0186361. In this method, the water-in-oil emulsion of the polymer may be prepared by in-situ polymerization in which the polymer emulsion is prepared directly from the constituent monomers by a so-called inverse emulsion polymerization technique in which a water-in-oil emulsion of an aqueous solution of the monomers is formed, in the presence of a catalytic amount of a free radical-yielding initiator so as to effect polymerization, the monomers being so chosen, and the process being so controlled, that the polymer product is in solution in the aqueous phase of a water-in-oil emulsion product. These polymers remain dissolved in the aqueous phase of the inverse emulsion, both during and after polymerisation. In addition, the following conditions apply:

1) The crosslinking monomer must contain 2 or more sites of unsaturation and be sufficiently-water soluble to react with aqueous acrylamide and neutralized or partially neutralised $AMPS^R$ monomers to produce a partially crosslinked copolymer that is still water soluble. The water solubility of the crosslinking agent is preferably at least 1% by weight of solution. Preferred cross linking agents are allyl sucrose, allyl pentaerythritol, and MBA. To retain solubility and to achieve optimum thickener/stabilizer efficiency, the molar ratio of crosslinking agent to the monomer mixture is critical; for MBA good results may be achieved within the range 0.06 to 1, preferably 0.08 to 0.7, the optimum being between 0.1 and 0.4 m.moles/mole, inclusive, of the monomer mixture. The precise quantity of crosslinking agent may be selected in dependence upon the proportion of AMPS in the monomer mix, larger proportions of AMPS possibly requiring slightly larger proportions of crosslinking agent.

2) The ratio, expressed as mole %, between the main monomers in the copolymer composition namely acrylamide/neutralized AMPS may be between 85/15 and 15/85, preferably between 70/30 and 30/70, more preferably between 65/35 and 35/65, especially between 60/40 and 40/60, inclusive.

3) Preferred neutralizing agents for AMPS are sodium or potassium hydroxide or water soluble/miscible amines of low toxicity (eg triethanolamine) or mixtures thereof.

4) Polymerisation may be carried out at a pH $\geq 5.5$, preferably $\geq 6.0$ and most preferably $\geq 6.5$, but $\leq 10.0$.

5) Oil in water emulsifiers or mixtures of emulsifiers, having an individual or composite HLB value $\geq 10$, preferably $\geq 11$ and most preferably $\geq 12$ and other additives such as inverse emulsion stabilizers, wetting agents, antifoams or combinations or mixtures thereof may be added to the water-in-oil emulsion. In an especially preferred process an inverse monomer emulsion is formed before polymerisation, in which case the oil in water emulsifier and other additives are added after the emulsification of the disperse and continuous phases. However, they then may be added at any time before, during or after the polymerisation process. Preferably, at least some, more preferably all, of the oil in water emulsifier is added after the polymerisation process.

6) The polymer solids content of the water-in-oil emulsion incorporated into the personal care or pharmaceutical preparation is preferably 35–60%, more preferably 40–50% by weight of the total weight of the emulsion.

Compositions embodying the invention may be prepared by incorporating the water in oil emulsion into the remaining components, whereupon the emulsion "inverts" to provide a continuous liquid phase comprising the aqueous medium of the emulsion and any liquid in the composition comprising water or miscible with water. Preferably, essentially all of the polymer is dissolved in the liquid phase. Topically acceptable adjuvants such as the liquid carrier, for example, an alcohol such as a glycol, optionally mixed with water, will then form part of the continuous liquid phase, other topically acceptable adjuvants which are insoluble or only partially soluble in the liquid phase being present in suspension or emulsion. A typical personal care product may contain, by weight of the total composition, up to 50% inclusive of any alcohol or glycol and may contain up to 5%, especially 1–5% inclusive, of a surface active agent.

BRIEF DESCRIPTION OF THE DRAWING

The accompanying drawing shows the variation of viscosity with Ph for a polymer (7) outside the invention and polymers (8), (9) and (11) embodying the invention.

DESCRIPTION OF PREFERRED EMBODIMENTS

Figure 1:
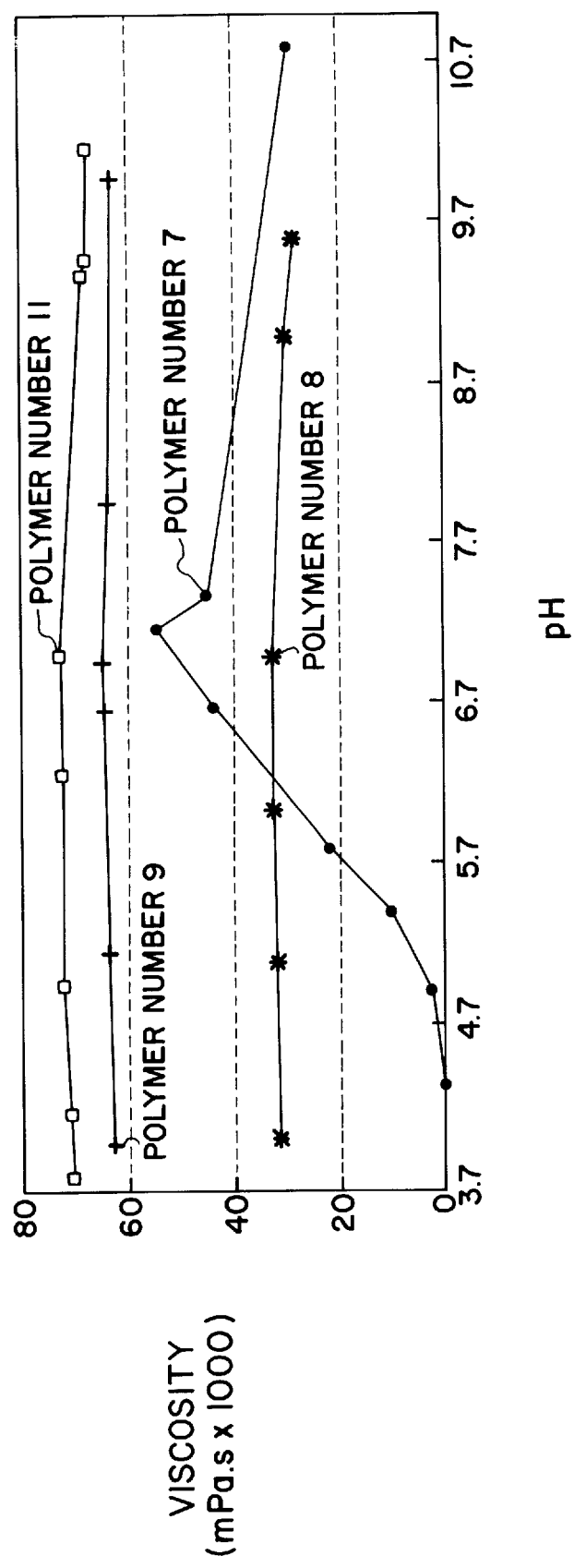

Using the method disclosed in Example 1 of EP-B-0186361, a series of polymers were prepared; their composition and properties are given in Table 1.

Experiments 1–7 inclusive, 10 and 12 in Table 1 show the thickening behaviour/solubility of polymer compositions similar to, but outside, the present invention. The thickening efficiency of polymers 1–6, which are homopolymers, is clearly inferior. Polymer 7, which is a copolymer, but contains sodium acrylate in place of the AMPS used in the compositions embodying the invention, meets the required standard of thickening efficiency (see Table 1). However, it gives an unstable solution viscosity over the preferred pH range 5.5 to 9 (see Graph 1). Polymers 10 and 12 contain too little and too much MBA respectively and neither meets the required standard of thickening efficiency (Table 1). As can be seen from Table 1 and Graph 1, only polymers 8, 9 and 11, embodying the present invention, meet the required standard of thickening efficiency (Table 1) and give a stable solution viscosity over the preferred pH range 5.5 to 9 (Graph 1).

A comparison between the same comonomer ratio and the degree of crosslinking can be seen in polymers 10, 11 and 12, in which the respective amounts of MBA in m moles per mole (and ppm by weight) of total monomer mix are 0.05 m moles (50 ppm), 0.22 m moles (248 ppm) and 1.1 m moles (1240 ppm). This comparison indicates that in order to thicken efficiently and retain solubility, the desirable level of MBA addition is above 0.05 and below 1.10 m.moles inclusive per mole of monomer mixture.

It is highly surprising that by controlling the amount of crosslinking agent between the range 0.12 to 2 milliequivalents per mole of total monomer units, an excellent thickening effect can be achieved without unwanted solids being present in the formulation and without incurring a "sticky" sensation to the skin on application, which occurs when too low a proportion of crosslinking agent is present.

TABLE 1

| Polymer Composition | Cross-linking m.moles (m.equivs) MBA per mole of monomer mix | Viscosity 0.85% Polymer Solution (Brookfield LVF Spindle 4, Speed 6) mPa · s | % Insoluble Material in the Polymer |
|---|---|---|---|
| 1. Sodium Polyacrylate | Zero (zero) | 14,900 | <0.1 |
| 2. Sodium Polyacrylate | 0.22 (0.44) | 22,000 | <0.1 |
| 3. Homopolymer of Acrylamide | Zero (zero) | <1,000 | <0.1 |
| 4. Homopolymer of Acrylamide | 0.22 (0.44) | <1,000 | <3.0 |
| 5. Homopolymer of Sodium Salt of AMPS | Zero (zero) | 1,700 | <0.1 |
| 6. Homopolymer of Sodium Salt of AMPS | 0.22 (0.44) | 13,300 | <0.1 |
| 7. Copolymer of 50 mole % Acrylamide 50 mole % Sodium Acrylate | 0.22 (0.44) | 53,000 | <0.1 |
| 8. Copolymer of 75 mole % Sodium Salt of AMPS 25 mole % Acrylamide | 0.22 (0.44) | 33,000 | <0.1 |
| 9. Copolymer of 25 mole % Sodium Salt of AMPS 75 mole % Acrylamide | 0.22 (0.44) | 65,000 | <0.5 |
| 10. Copolymer of 40 mole % Sodium Salt of AMPS 60 mole % Acrylamide | 0.05 (0.10) | 18,000 | <0.01 |
| 11. Copolymer of 40 mole % Sodium Salt of AMPS 60 mole % Acrylamide | 0.22 (0.44) | 76,000 | <0.01 |
| 12. Copolymer 40 mole % Sodium Salt of AMPS 60 mole % Acrylamide | 1.1 (2.2) | 10,000 | <0.5 |

Polymer 11 of Table 1 corresponds to the copolymer described in Example 1. All viscosity and pH measurements mentioned in the examples were carried out at 25° C.

EXAMPLE 1

BEST METHOD OF PREPARATION

Using the method described in Example 1 of EP-B-0186361 with an ammonium persulphate/sodium metabisulphite redox system a water in oil inverse emulsion was prepared from the sodium salt of 2-acrylamido-2-methylpropanesulphonic acid and acrylamide, crosslinked with N,N$^1$-methylenebisacrylamide. Polymer composition was 60 mole % acrylamide, 40 mole % sodium salt of AMPS, crosslinked with 0.22 m.moles of MBA per mole monomer mixture. The polymerisation was carried out at pH 7.0. To the finished inverse-emulsion was added 5% (based on the weight of the total inverse emulsion) of a mixture consisting 20% by weight of an antifoam and 80% by weight of an ethoxylated higher alcohol surfactant having an HLB of 12.5.

The finished inverse emulsion had the following properties:

| | | |
|---|---|---|
| 1. | Polymer content | 41% |
| 2. | Inverse emulsion viscosity | 3,200 mPa · s |
| 3. | Inverse emulsion pH | 6.9 |
| 4. | 0.85% Polymer solution viscosity in deionised water | 76,000 mPa · s |
| 5. | pH of 1.0% solution | 7.3 |
| 6. | % insoluble material | <0.01 |

USE EXAMPLES

The inverse emulsion from Example 1 was used for the following thickening experiments.

A. EXAMPLES OF PERSONAL CARE PRODUCTS

1. Thickening of water alcohol mixtures (necessary for preparation of personal care gels).

| | | |
|---|---|---|
| [a] | 1.2% Polymer solution viscosity in deionised water | 100,000 mPa · s |
| [b] | 1.2% Polymer solution viscosity in; 80% Water 20% Ethanol (90°) | 100,000 mPa · s |
| [c] | 1.2% Polymer solution viscosity in; 50% Water 50% Ethanol (90°) | 100,000 mPa · s |

2. Thickening of water glycol mixtures

| | | |
|---|---|---|
| [a] | 1.2% Polymer solution viscosity in deionised water | 100,000 mPa · s |
| | 1.2% Polymer solution viscosity in; 70% Water 30% Propylene glycol | 100,000 mPa · s |

3. Emulsion stabilisation (necessary for the preparation of personal care cream)

Formulation:

| | | Parts by weight |
|---|---|---|
| 1. | Water | 86.5 |
| 2. | Inverse emulsion from Example 1 | 3.0 (Polymer 1.23) |
| 3. | SEPICIDE C1 | 0.2 |
| 4. | SEPICIDE HB | 0.3 |
| 5. | Oil | 10.0 |

Procedure: Mixed items 2, 3 and 4 in item 1, using a high speed mixer then mixed item 5.
RESULTS

| | Oil | | |
|---|---|---|---|
| | Dimethicone | Sweet Almond Oil | Cetearyl Octanoate |
| Initial viscosity | >100,000 mPa · s | >100,000 mPa · s | >100,000 mPa · s |
| 1 month @ room temp. | stable | stable | stable |
| 1 month @ 50° C. | stable | stable | stable |

4. Preparation of an after-shave lotion

| | Parts by weight |
|---|---|
| Water | 82.80 |
| Inverse emulsion from Example 1 | 1.50 (Polymer 0.62) |
| Ethanol 95° | 10.00 |
| MICROPEARL M 100 (Polymethyl methacrylate powder) | 5.00 |
| Sepicide C1 (Preservative) | 0.50 |
| SCALA 5610 (Perfume) | 0.20 |

Procedure: Homogenised all ingredients with a higher shear mixer.

| Properties/Characteristics: | |
|---|---|
| Appearance | Smooth white gel/emulsion |
| pH | 6.5 |
| Viscosity | 12,000 mPa · s |
| Stability | Stable at room temp. and at 50° C. for more than four weeks. |

5. Preparation of oil in water cream

| | | Parts by weight |
|---|---|---|
| 1. | SIMULSOL 165 (self-emulsifying base for creams) | 5.00 |
| 2. | LANOL 1688 (non-greasy ester) | 20.00 |
| 3. | LANOL P (stabilizer) | 1.00 |
| 4. | Water | 71.00 |
| 5. | Inverse emulsion from Example 1 | 2.50 (Polymer 1.03) |
| 6. | SEPICIDE HB (Preservative) | 0.30 |
| 7. | SEPICIDE C1 (Preservative) | 0.20 |

Procedure: Heated items 1, 2 and 3 to 70° C. and mixed in item 4, preheated to 75° C., using a high speed mixer. Cooled to 55° C. and incorporated item 5 using the high speed mixer. Cooled to 45° C. and incorporated items 6 and 7 using the high speed mixer.

| Properties/Characteristics: | |
|---|---|
| Appearance | Smooth ivory coloured cream |
| pH | 6.0 |
| Viscosity | 100,000 mPa · s |
| Stability | Stable at room temp. and at 50° C. for more than four weeks. |

6. Preparation of Massage Gel

| | | Parts by weight |
|---|---|---|
| 1. | Inverse emulsion from Example 1 | 3.50 (Polymer 1.44) |
| 2. | Water | 20.00 |
| 3. | BLUE 512/12 (1%) | |

|   | Parts by weight |
|---|---|
| (Colorant; 2 drops/100 g) | |
| 4. Water | 61.40 |
| 5. Menthol | 0.10 |
| 6. Ethanol 95° | 10.00 |
| 7. Silicone oil (350 CS) | 5.00 |

Procedure: Using a high speed mixer, mixed item 1 in item 2 and followed by mixing items 3 dissolved in item 4 and item 5 dissolved in item 6. Then mixed in item 7.

| Properties/Characteristics: | |
|---|---|
| Appearance | Smooth blue coloured translucent gel |
| pH | 5.5 |
| Viscosity | 100,000 mPa · s |
| Stability | Stable at room temp. and at 50° C. for more than four weeks |

B. EXAMPLES OF PHARMACEUTICAL PREPARATIONS

7. Preparation of Rubefacient Gel

|   |   | Parts by weight |
|---|---|---|
| 1. | Water | 62.00 |
| 2. | Inverse emulsion from Example 1 | 2.00 (Polymer 0.82) |
| 3. | Methyl Nicotine | 0.50 |
| 4. | SEPICIDE CI | 0.20 |
| 5. | Glycol Salicylate | 10.00 |
| 6. | Ethanol 95° | 25.00 |
| 7. | SEPICIDE HB | 0.30 |

Procedure: Dissolved items 3 and 4 in item 1 and mixed in item 2 with a high speed stirrer. Mixed items 5, 6 and 7 together and then added to stirring mixture of item 1–4.

| Characteristics: | |
|---|---|
| pH | about 5.5 |
| Viscosity | about 11,000 mPa · s |
| Appearance | White gel |

8. Preparation of Keratosic Skin Treatment Cream

| 1. MONTANOL 68 Hazelnut oil (cetearyl glucoside) | 5.00 |
|---|---|
| 2. Wheat germ oil | 3.00 |
| 3. Paraffin oil | 7.00 |
| 4. Shea Tree Butter | 1.00 |
| 5. LIPACID PCO (palmitoyl hydrolysed collagen) | 2.00 |
| 6. Water | 69.50 |
| 7. Inverse emulsion from Example 1 | 1.00 (Polymer 0.41) |
| 8. SEPICIDE CI | 0.20 |
| 9. SEPICIDE HB | 0.30 |
| 10. Urea | 10.00 |
| 11. Ammonium Chloride | 1.00 |
| 12. Perfume | |
| 13. Triethanolamine to pH 5.0 | |

Procedure: Melted and dissolved items 1–5 at 70° C. Emulsified items 1–5 in 6 at 70° C. Mixed in item 7 at 60° C. with high speed stirring. At 30° C. mixed in items 8–12 with stirring. Adjusted the pH with item 13.

| Characteristics: | |
|---|---|
| pH | 5.0 |
| Viscosity | about 40,000 mPa · s |
| Appearance | Beige Cream |

9. Preparation of Antibiotic Gel

|   | Parts by weight |
|---|---|
| 1. Water | 79.5 |
| 2. SEPICIDE CI | 0.20 |
| 3. Inverse emulsion from Example 1 | 3.00 (Polymer 1.23) |
| 4. SEPICIDE HB | 0.30 |
| 5. Erythromycin | 2.00 |
| 6. Ethanol 95° | 15.00 |

Procedure: Mix items 1 and 2 and add item 3 with high speed stirring. Add item 4 and 5 dissolved in 6 with high speed stirring.

| Characteristics: | |
|---|---|
| pH | about 9.1 |
| Viscosity | about 75,000 mPa · s |
| Appearance | White gel |

10. Preparation of Anti-Acne Gel

|   | Parts by weight |
|---|---|
| 1. Water | 66.475 |
| 2. SEPICIDE CI | 0.2 |
| 3. Inverse emulsion from Example 1 | 3.00 (Polymer 1.23) |
| 4. Retinoic Acid | 0.025 |
| 5. SEPICIDE HB | 0.30 |
| 6. Ethanol 95° | 30.00 |

Procedure: Mix items 1, 2 and 3 with high speed stirring. Add items 4 and 5 dissolved in 6 with high speed stirring.

| Characteristics: | |
|---|---|
| pH | about 6.8 |
| Viscosity | about 85,000 mPa · s |
| Appearance | Yellow opaque gel |
| SEPICIDE - Registered Trade Mark of SEPPIC | Paris |
| MICROPEARL - Registered Trade Mark of MATSUMOTO | Japan |
| SIMULSOL - Registered Trade Mark of SEPPIC | Paris |
| LANOL - Registered Trade Mark of SEPPIC | Paris |
| COLORANT 512/12, supplied by WACKER | France |

-continued

| Characteristics: | |
|---|---|
| PERFUME SCALA 5610, supplied by PFIZER | USA |
| MONTANOL - Trade Mark of SEPPIC | Paris |
| LIPACID PCO - Trade Mark of GIRAUDAN | France |

We claim:

1. A method of preparing a composition for topical application, which method comprises admixing a topically acceptable, liquid-containing, formulation containing a topically acceptable adjuvant with a water in oil emulsion containing a polymeric material, at least 98% of the polymeric material in the emulsion being water soluble, which polymeric material consists of units derived from monomer components (a) acrylamide, (b) 2-acrylamido-2-methylpropanesulphonic acid and (c) a polyfunctional monomer which is allyl sucrose, allyl pentaerythritol or methylene-bisacrylamide for cross linking with said monomer components (a) and (b), which said units derived from monomer components (a) and (b) are present in the polymeric material in a molar ratio (a)/(b) of from 85/15 to 15/85 inclusive and which polyfunctional monomer is present in an amount of from 0.12 to 2 milliequivalents inclusive per mole of total monomer units, at least some of the 2-acrylamido-2-methylpropanesulphonic acid units being in the form of a neutral salt thereof such that the water phase of the water in oil emulsion has a pH of at least 5.5, whereby on admixing the topically acceptable liquid-containing formulation containing a topically acceptable adjuvant with the said water in oil emulsion, an increase in viscosity of said formulation occurs so as to thicken said formulation and said formulation being so thickened that it has an essentially constant viscosity over a pH range of the said composition from 5.5 to 9.

2. A method according to claim 1, wherein the water in oil emulsion has a polymer content and a pH at which at least 98% of the polymeric material is dissolved in the water phase of the water in oil emulsion.

3. A method according to claim 1, wherein the polyfunctional monomer is methylene-bisacrylamide.

4. A method according to claim 3, wherein the methylene-bisacrylamide is present in the water in oil emulsion in an amount of from 0.08 to 0.7 m.mole per 1 mole of the total of the monomer units (a) and (b).

5. A method according to claim 4, wherein the methylene-bisacrylamide is present in the water in oil emulsion in an amount of from 0.1 to 0.4 m.mole per 1 mole of the total of the monomer units (a) and (b).

6. A method according to claim 1, wherein the water in oil emulsion contains, as a neutralizing agent, at least one of sodium and potassium hydroxides and water soluble and water miscible amines.

7. A method according to claim 1, wherein the composition for topical application additionally contains an oil in water emulsifying agent comprising at least one emulsifier and having a hydrophile lipophile balance of at least 10.

8. A method according to claim 1, wherein the topically acceptable adjuvant comprises an alcohol.

9. A method according to claim 1, which includes the preliminary step of preparing the water in oil emulsion containing the polymeric material, at least 98% of the polymeric material in the emulsion being water soluble, which preliminary step comprises forming, with the assistance of a water in oil emulsifier and in the presence of a free radical-yielding initiator, a water in oil emulsion of a monomer composition, in which water in oil emulsion the concentration of total monomer, by weight of the total of the water in oil emulsion and monomer composition, is at least 30 weight % and which monomer composition consists of monomer components (a) acrylamide, (b) 2-acrylamido-2-methylpropanesulphonic acid and (c) a polyfunctional monomer which is allyl sucrose, allyl pentaerythritol or methylene-bisacrylamide for cross linking with said monomer components (a) and (b), which monomer components (a) and (b) are present in the monomer composition in a molar ratio (a)/(b) of from 85/15 to 15/85 inclusive and which polyfunctional monomer is present in the monomer composition in an amount of 0.12 to 2 milliequivalents inclusive per mole of total monomer units, at least some of the 2-acrylamido-2-methylpropanesulphonic acid being in the form of a neutral salt thereof such that the water phase of the water in oil emulsion containing the monomer composition has a pH of at least 5.5, and subjecting the monomer composition to inverse emulsion polymerization in which the free radical-yielding initiator initiates polymerization of the monomers to form a solution of the polymer in the water phase of a water in oil emulsion.

10. A composition for topical application comprising
    a topically acceptable liquid phase comprising a water phase,
    a polymeric material at least 98% of which is water soluble, which polymeric material consists of units derived from monomer components (a) acrylamide, (b) 2-acrylamido-2-methylpropanesulphonic acid and (c) a polyfunctional monomer which is allyl sucrose, allyl pentaerythritol or methylene-bisacrylamide for cross linking with said monomer components (a) and (b), which said units derived from monomer components (a) and (b) are present in the polymer material in a molar ratio (a)/(b) of from 85/15 to 15/85 inclusive and which polyfunctional monomer is present in an amount of from 0.12 to 2 milliequivalents inclusive per mole of total monomer units, an oil phase, a water in oil emulsifier, an oil in water emulsifier, and a topically acceptable adjuvant, optionally forming part of the liquid phase, and whereby said polymeric material serves to thicken the composition and render essentially constant the viscosity of the composition over a pH range of from 5.5 to 9.

11. A personal care product which is a composition according to claim 10, wherein the topically acceptable liquid phase additionally comprises an alcohol.

12. A pharmaceutical composition for topical application which is a composition according to claim 10, which additionally contains a pharmaceutically active component.

13. A composition according to claim 10 which has a pH of at least 5.

14. A composition according to claim 10 which is a cream.

15. A composition according to claim 10 which is a gel.

16. A water in oil emulsion containing a polymeric material, at least 98% of the polymeric material in the emulsion being water soluble, which polymeric material consists of units derived from monomer components (a) acrylamide, (b) 2-acrylamido-2-methyl-propanesulphonic acid and (c) a polyfunctional monomer which is allyl sucrose, allyl pentaerythritol or methylene-bisacrylamide for cross linking with said monomer components (a) and (b), which said units derived from monomer components (a) and (b) are present in the polymeric material in a molar ratio (a)/(b) of from 85/15 to 15/85 inclusive and which polyfunctional monomer is present in an amount of from 0.12 to 2 milliequivalents inclusive per mole of total monomer units, at least some of the 2-acrylamido-2- methylpropanesulphonic acid units being in the form of a neutral salt thereof such that the water phase of the water in oil emulsion has a pH of at least 5.5, which water in oil emulsion is capable, on admixture with a topically acceptable liquid-containing formulation of increasing the viscosity of said formulation to provide a thickened composition having an essentially constant viscosity over a pH range of the composition of from 5.5 to 9.

17. A water in oil emulsion according to claim 16, which has a polymer content and a pH at which at least 98% of the polymeric material is dissolved in the water phase.

18. A water oil emulsion according to claim 16, wherein the polyfunctional monomer is methylenebisacrylamide.

19. A water in oil emulsion according to claim 21, wherein the methylene-bisacrylamide is present in the water in oil emulsion in an amount of from 0.08 to 1 m.mole per 1 mole of the total of the monomer units (a) and (b).

20. A water in oil emulsion according to claim 19, wherein the methylene-bisacrylamide is present in the water in oil emulsion in an amount of from 0.1 to 0.4 mole per 1 mole of the total of the monomer units (a) and (b).

21. A water in oil emulsion according to claim 16, containing, as a neutralizing agent, at least one of sodium and potassium hydroxides and water soluble and water miscible amines.

22. A water in oil emulsion according to claim 16, which additionally contains an oil in water emulsifying agent comprising at least one emulsifier and having a hydrophile lipophile balance of at least 10.

23. A method of preparing a water in oil emulsion containing a polymeric material, at least 98% of the polymeric material in the emulsion being water soluble, which process comprises forming, with the assistance of a water in oil emulsifier and in the presence of a free radical-yielding initiator, a water in oil emulsion of a monomer composition, in which water in oil emulsion the concentration of total monomer, by weight of the total of the water in oil emulsion and monomer composition, is at least 30 weight % and which monomer composition consists of monomer components (a) acrylamide, (b) 2-acrylamido-2-methylpropanesulphonic acid and (c) a polyfunctional monomer which is allyl sucrose, allyl pentaerythritol or methylene-bisacrylamide for cross linking with said monomer components (a) and (b), which monomer components (a) and (b) are present in the monomer composition in a molar ratio (a)/(b) of from 85/15 to 15/85 inclusive and which polyfunctional monomer is present in the monomer composition in an amount of 0.12 to 2 milliequivalents inclusive per mole of total monomer units, at least some of the 2-acrylamido-2-methylpropanesulphonic acid being in the form of a neutral salt thereof such that the water phase of the water in oil emulsion containing the monomer composition has a pH of at least 5.5, and subjecting the monomer composition to inverse emulsion polymerization in which the free radical-yielding initiator initiates polymerization of the monomers to form a solution of the polymer in the water phase of a water-in-oil emulsion, which water in oil emulsion is capable, on admixture with a topically acceptable liquid-containing formulation of increasing the viscosity of said formulation to provide a thickened composition having an essentially constant viscosity over a pH range of the composition of from 5.5 to 9.

* * * * *